United States Patent
Wang et al.

(10) Patent No.: US 12,270,885 B2
(45) Date of Patent: Apr. 8, 2025

(54) ACCELERATED HASTE FOR PACE TRIGGERING

(71) Applicant: Siemens Healthcare GmbH, Erlangen (DE)

(72) Inventors: Yu Yu Wang, Shenzhen (CN); Fang Dong, Shenzhen (CN)

(73) Assignee: Siemens Healthineers AG, Erlangen (DE)

(*) Notice: Subject to any disclaimer, the term of this patent is extended or adjusted under 35 U.S.C. 154(b) by 756 days.

(21) Appl. No.: 17/405,475

(22) Filed: Aug. 18, 2021

(65) Prior Publication Data
US 2022/0057466 A1 Feb. 24, 2022

(30) Foreign Application Priority Data
Aug. 19, 2020 (CN) .......................... 202010836538.1

(51) Int. Cl.
*G01R 33/567* (2006.01)
*A61B 5/055* (2006.01)
(Continued)

(52) U.S. Cl.
CPC .......... *G01R 33/5676* (2013.01); *A61B 5/055* (2013.01); *G01R 33/5615* (2013.01); *G01R 33/56509* (2013.01)

(58) Field of Classification Search
CPC ............ G01R 33/5676; G01R 33/5615; G01R 33/56509; A61B 5/055
See application file for complete search history.

(56) References Cited

U.S. PATENT DOCUMENTS

| | | |
|---|---|---|
| 4,717,879 A | 1/1988 | Riederer et al. |
| 5,420,509 A | 5/1995 | Takai |

(Continued)

FOREIGN PATENT DOCUMENTS

| | | |
|---|---|---|
| CN | 102680930 A | 9/2012 |
| CN | 105785297 A | 7/2016 |

(Continued)

OTHER PUBLICATIONS

Kim, B. S., Kim, J. H., Choi, G. M., Kim, S. H., Park, J. K., Song, B. C., & Kang, W. (2008). Comparison of three free-breathing T2-weighted MRI sequences in the evaluation of focal liver lesions. American Journal of Roentgenology, 190(1), W19-W27. (Year: 2008).*

(Continued)

*Primary Examiner* — Keith M Raymond
*Assistant Examiner* — Johnathan Maynard
(74) *Attorney, Agent, or Firm* — Banner & Witcoff Ltd.

(57) ABSTRACT

The disclosure relates to magnetic resonance imaging triggered by a prospective acquisition correction sequence. The technique comprises determining repetition time and an acquisition window time of a single-shot fast spin echo sequence; determining the maximum imaging layer number N in each physiological movement cycle on the basis of the acquisition window time and the repetition time, where N is a positive integer greater than or equal to 2; and enabling the single-shot fast spin echo sequence to obtain M layers of imaging data within at least one acquisition window time when the prospective acquisition correction sequence generates a trigger signal, where M is a positive integer greater than or equal to 2 and less than or equal to N. According to the present disclosure, a plurality of layers of imaging data are obtained within a single acquisition window time, thereby increasing a scanning speed and shortening imaging time.

18 Claims, 5 Drawing Sheets

(51) Int. Cl.
*G01R 33/561* (2006.01)
*G01R 33/565* (2006.01)

(56) References Cited

U.S. PATENT DOCUMENTS

| | | |
|---|---|---|
| 2002/0095085 A1 | 7/2002 | Saranathan et al. |
| 2004/0263166 A1 | 12/2004 | Kluge |
| 2011/0130644 A1* | 6/2011 | Stemmer ............ G01R 33/5676 600/410 |
| 2011/0221439 A1 | 9/2011 | Posse |
| 2012/0229136 A1* | 9/2012 | Stemmer ............ G01R 33/5659 324/307 |
| 2012/0235681 A1 | 9/2012 | Stemmer |
| 2012/0271155 A1* | 10/2012 | Stemmer ............ G01R 33/5676 600/413 |
| 2016/0077180 A1 | 3/2016 | Beck |
| 2016/0178719 A1 | 6/2016 | Liu et al. |
| 2023/0252622 A1 | 8/2023 | Nielsen et al. |

FOREIGN PATENT DOCUMENTS

| | | |
|---|---|---|
| CN | 106597337 A | 4/2017 |
| CN | 107367703 A | 11/2017 |
| CN | 108652624 A | 10/2018 |
| CN | 109061533 A | 12/2018 |
| DE | 19616388 A1 | 11/1997 |
| GB | 2586119 A | 2/2021 |
| JP | H0871060 A | 3/1996 |
| WO | 2014154544 A1 | 10/2014 |

OTHER PUBLICATIONS

Siemens (2015). Syngo MR E11 Operator Manual—Body. (Year: 2015).*

Moroi, T., Mizuuchi, N., Maruyama, K., Imura, C., Isobe, I., Usagawa, T., & Iriguchi, N. (May 2007). Abdominal T2-Weighted Imaging by Free-Breath PACE with a 3.0 T MRI System. In 2007 IEEE/ICME International Conference on Complex Medical Engineering (pp. 740-743). IEEE. (Year: 2007).*

Green, J. D., Flewitt, J. A., Voehringer, M., & Friedrich, M. G. (2008). 1078 T1-weighted, navigator-gated HASTE for the monitoring of the early enhancement of myocardium. Journal of Cardiovascular Magnetic Resonance, 10, 1-2. (Year: 2008).*

Thesen S et al: "Prospective Acquisition Correction for Head Motion with Image-Basedtracking For Real-Time FMRI", Magnetic Resonance In Medicine, John Wiley & Sons, Inc, vol. 44, No. 3, pp. 457-465, XP000951988, ISSN: 0740-3194, DOI: 10.1002/1522-2594(200009)44:3 457: AIDMRM173.0.C0;2-R; 2000.

Dong Fang "Artifacts Correction with Navigator Echo in MRI" 2014 Graduate Candidate Dissertation, E060-17, 2014. (w/English Abstract).

* cited by examiner

ACCELERATED HASTE FOR PACE TRIGGERING

CROSS-REFERENCE TO RELATED APPLICATIONS

The present application claims the benefit of the filing date of China patent application no. CN 202010836538.1, filed on Aug. 19, 2020, the contents of which are incorporated herein by reference in their entirety.

TECHNICAL FIELD

The disclosure relates to the technical field of medical instruments and, in particular, to a techniques for magnetic resonance imaging triggered by a prospective acquisition correction (PACE) sequence.

BACKGROUND

Magnetic resonance imaging (MRI) is a biomagnetism nuclear spin imaging technology that has developed rapidly with the development of computer technologies, electronic circuit technologies, and superconductor technologies. The technology uses magnetic fields and radio frequency pulses to make precessing hydrogen nuclei (that is, H+) in human tissues vibrate to generate radio frequency signals, which are imaged by being processed by computers. When placed in the magnetic fields, objects are irradiated with appropriate electromagnetic waves, so as to resonate, and then electromagnetic waves released by the objects are analyzed, making it possible to know the positions and types of nuclei constituting the objects, on the basis of which accurate stereoscopic images inside the objects can be drawn. For example, one animation of a continuous slice obtained of the human brain starting from the top of the head to the feet can be scanned through magnetic resonance imaging.

Single-shot fast spin echo sequences are high-speed magnetic resonance imaging sequences, and are applicable to many clinical applications, especially motion sensitive imaging applications. A layer of complete images of imaging objects can be obtained by only shooting a single-shot fast spin echo sequence once. Generally, the single-shot fast spin echo sequences comprise half-Fourier acquisition single-shot turbo spin-echo (HASTE) sequences, turbo spin echo-single-shot (TSE-SSH) sequences, single shot fast spin echo (SS-FSE) sequences, etc. During magnetic resonance imaging of the thorax and abdomen, due to the influence of physiological movement (such as respiratory movement of patients), artifacts often appear in the images. Therefore, it is necessary to monitor the physiological movement of the objects under examination, so as to eliminate the artifacts caused by same. By combining a trigger mechanism of a PACE sequence, a single-shot fast spin echo sequence can obtain imaged images with almost no motion artifacts.

In the current single-shot fast spin echo sequence, after trigger signals are received from the PACE sequence, the single-shot fast spin echo sequence obtains a single layer of imaging data in each physiological movement cycle, and therefore requires a long time for imaging.

SUMMARY

Embodiments of the present disclosure propose a method and an apparatus for magnetic resonance imaging triggered by a prospective acquisition correction sequence.

The technical solution of the embodiments of the present disclosure is as follows.

A method for magnetic resonance imaging triggered by a PACE sequence comprises:
  determining repetition time and an acquisition window time of a single-shot fast spin echo sequence;
  determining the maximum imaging layer number N in each physiological movement cycle on the basis of the acquisition window time and the repetition time, where N is a positive integer greater than or equal to 2; and
  enabling the single-shot fast spin echo sequence to obtain M layers of imaging data within at least one acquisition window time when the PACE sequence generates a trigger signal, where M is a positive integer greater than or equal to 2 and less than or equal to N.

It may be seen that unlike conventional techniques, in which only a single layer of imaged images are obtained within the acquisition window time, in the embodiments of the present disclosure, a plurality of layers of imaging data may be obtained within the acquisition window time, thereby improving the scanning speed and shortening imaging time.

In an embodiment, the determining an acquisition window time comprises:
  applying the PACE sequence to detect a physiological signal curve;
  determining the physiological movement cycle on the basis of the physiological signal curve; and
  determining the acquisition window time on the basis of the physiological movement cycle.

Therefore, in the embodiment of the present disclosure, the acquisition window time may be determined on the basis of the physiological signal curve detected by the PACE sequence, thereby improving the accuracy of the acquisition window time.

In an embodiment, the determining the maximum imaging layer number N in each physiological movement cycle on the basis of the acquisition window time and the repetition time comprises:
  determining the maximum imaging layer number N, where N=int(TA/TR); and
  where TR is the repetition time, TA is the acquisition window time, and int(TA/TR) is a rounded value of (TA/TR).

It may be seen that, in the embodiment of the present disclosure, the maximum imaging layer number may be quickly determined on the basis of the acquisition window time and the repetition time.

In an embodiment, the enabling the single-shot fast spin echo sequence to obtain M layers of imaging data within at least one acquisition window time comprises:
  determining the number K of physiological movement cycles when a predetermined total imaging layer number L is not divisible by M, where K=(int(L/M)+1), and int(L/M) is a rounded value of (L/M); enabling the single-shot fast spin echo sequence to obtain M layers of imaging data within an acquisition window time of each physiological movement cycle from the first physiological movement cycle to a $(K-1)^{th}$ physiological movement cycle; and enabling the single-shot fast spin echo sequence to obtain $(L-(K-1)*M)$ layers of imaging data in a $K^{th}$ physiological movement cycle; or
  determining the number K of physiological movement cycles when a predetermined total imaging layer number L is divisible by M, where K=(L/M); and enabling the single-shot fast spin echo sequence to obtain M layers of imaging data within an acquisition window time of each physiological movement cycle from the first physiological movement cycle to a $K^{th}$ physiological movement cycle.

Therefore, according to the embodiment of the present disclosure, different processing manners of acquisition of a plurality of layers of imaging data within the acquisition window time are realized in consideration of different conditions of whether the total imaging layer number is divisible by M.

An apparatus for magnetic resonance imaging triggered by a PACE sequence comprises:
  a time determination module configured to determine repetition time and an acquisition window time of a single-shot fast spin echo sequence;
  a maximum imaging layer number determination module configured to determine the maximum imaging layer number N in each physiological movement cycle on the basis of the acquisition window time and the repetition time, where N is a positive integer greater than or equal to 2; and
  an imaging data obtaining module (e.g. image acquisition circuitry) configured to enable the single-shot fast spin echo sequence to obtain M layers of imaging data within at least one acquisition window time when the PACE sequence generates a trigger signal, where M is a positive integer greater than or equal to 2 and less than or equal to N.

It may be seen that unlike conventional techniques, in which only a single layer of imaged images is obtained within the acquisition window time, in the embodiment of the present disclosure, a plurality of layers of imaging data may be obtained within the acquisition window time, thereby improving the scanning speed and shortening imaging time.

In an embodiment, the time determination module is configured to apply the PACE sequence to detect a physiological signal curve; determine the physiological movement cycle on the basis of the physiological signal curve; and determine the acquisition window time on the basis of the physiological movement cycle.

Therefore, in the embodiment of the present disclosure, the acquisition window time may be determined on the basis of the physiological signal curve detected by the PACE sequence, thereby improving the accuracy of the acquisition window time.

In an embodiment, the maximum imaging layer number determination module is configured to determine the maximum imaging layer number N, where N=int(TA/TR); and where TR is the repetition time, TA is the acquisition window time, and int(TA/TR) is a rounded value of (TA/TR).

It may be seen that, in the embodiment of the present disclosure, the maximum imaging layer number may be quickly determined on the basis of the acquisition window time and the repetition time.

In an embodiment, the imaging data obtaining module is configured to determine the number K of physiological movement cycles when a predetermined total imaging layer number L is not divisible by M, where K=(int(L/M)+1), and int(L/M) is a rounded value of (L/M); enable the single-shot fast spin echo sequence to obtain M layers of imaging data within an acquisition window time of each physiological movement cycle from the first physiological movement cycle to a $(K-1)^{th}$ physiological movement cycle; and enable the single-shot fast spin echo sequence to obtain (L−(K−1)*M) layers of imaging data in a $K^{th}$ physiological movement cycle; or determine the number K of physiological movement cycles when a predetermined total imaging layer number L is divisible by M, where K=(L/M); and enable the single-shot fast spin echo sequence to obtain M layers of imaging data within an acquisition window time of each physiological movement cycle from the first physiological movement cycle to a $K^{th}$ physiological movement cycle.

Therefore, according to the embodiment of the present disclosure, different processing manners of acquisition of a plurality of layers of imaging data within the acquisition window time are realized in consideration of different conditions of whether the total imaging layer number is divisible by M.

A control host (e.g. a control computer, controller, control circuitry, etc.) of a magnetic resonance imaging system comprises: a memory, and a processor, wherein an application program executable by the processor is stored in the memory, and is used for causing the processor to execute the method for magnetic resonance imaging triggered by a PACE sequence as described in any of the above.

It may be seen that the control host in the embodiment of the present disclosure may control the obtaining of a plurality of layers of imaging data within the acquisition window time, thereby increasing the scanning speed and shortening the imaging time.

A computer-readable storage medium (e.g. a non-transitory computer-readable medium) stores a computer program thereon, and the computer program, when executed by a processor, implements the method for magnetic resonance imaging triggered by a PACE sequence as described in any of the above.

Therefore, the embodiment of the present disclosure further proposes the computer-readable storage medium, which may control the obtaining of a plurality of layers of imaging data within the acquisition window time, thereby increasing the scanning speed and shortening the imaging time.

BRIEF DESCRIPTION OF THE DRAWINGS/FIGURES

Embodiments of the present disclosure are described in detail below with reference to the accompanying drawings, to give those skilled in the art a clearer understanding of the abovementioned and other features and advantages of the present disclosure.

Figure 1:
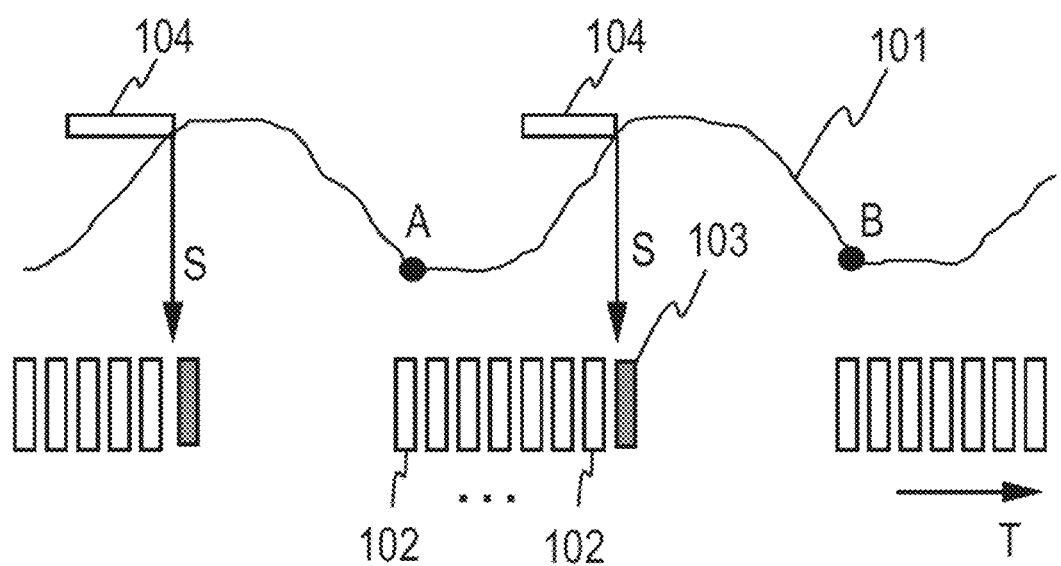
FIG. 1 is a schematic diagram of obtaining imaging data by a HASTE sequence triggered by a PACE sequence in the prior art.

Reference numerals in the accompanying drawings are as follows:

| | |
|---|---|
| 101 | Physiological signal curve |
| 102 | Navigation sequence |
| 103 | Single layer of imaging data |
| 104 | Receiving window |
| 200 | Method for magnetic resonance imaging triggered by a PACE sequence |
| 201 to 203 | Steps |
| 300 | Execution process of obtaining a single layer of imaging data by a HASTE sequence |
| 301 | Radio frequency excitation pulse |
| 302 | Radio frequency echo refocusing pulse |
| 401 | First single layer of imaging data |
| 402 | Second single layer of imaging data |
| 403 | Third single layer of imaging data |
| 404 | Fourth single layer of imaging data |
| 500 | Apparatus for magnetic resonance imaging triggered by a PACE sequence |
| 501 | Time determination module |
| 502 | Maximum imaging layer number determination module |
| 503 | Imaging data obtaining module |
| 600 | Control host of a magnetic resonance imaging system |
| 601 | Memory |
| 602 | Processor |

DETAILED DESCRIPTION

In order to make the technical solution and advantages of the present disclosure clearer, the present disclosure is further illustrated in detail below in conjunction with the accompanying drawings and embodiments. It should be understood that the specific embodiments described herein are merely used for illustratively describing the present disclosure, but not limiting the scope of protection of the present disclosure.

In order to be concise and intuitive in the description, the solution of the present disclosure is explained by describing several exemplary embodiments below. A large number of details in the embodiments are merely used to help understand the solution of the present disclosure. However, it is obvious that the implementation of the technical solution of the present disclosure may not be limited to these details. In order to prevent the solution of the present disclosure from being unnecessarily obscured, some embodiments are not described in detail, but only the framework thereof is given. Hereinafter, "including" means "including but not limited to", "according to" means "at least according to . . . , but not limited to only according to . . . ". When the number of a component is not specified in the following, it means that the number of the component may be one or more, or may be understood as at least one.

PACE technology, as a respiratory gating technology, may effectively remove respiratory artifacts. When the PACE technology is applied to respiratory gating, a small-angle excited gradient echo sequence is scanned continuously, two-dimensional images with low resolution are acquired, and trigger points are obtained to trigger scanning of imaging sequences such as a single-shot fast spin echo sequence. In a current single-shot fast spin echo sequence, after a trigger signal is received from a PACE sequence, the single-shot fast spin echo sequence obtains a single layer of imaging data in a single physiological movement cycle. However, only a single layer of imaging data can be obtained in the single physiological movement cycle, and consequently, the scanning speed is slow and imaging time is long.

The single-shot fast spin echo sequence being implemented as a HASTE sequence is taken as an example for description.

FIG. 1 is a schematic diagram of obtaining imaging data by a HASTE sequence triggered by a PACE sequence in the prior art. It may be seen from FIG. 1 that on a timeline T, a physiological signal curve 101 comprising a plurality of physiological movement cycles (such as respiratory cycles) extends periodically. In each physiological movement cycle, before the PACE sequence sends a trigger signal, a navigation sequence 102 is executed.

When a receiving window 104 of the PACE sequence comes into contact with the physiological signal curve 101, the PACE sequence sends the trigger signal as shown by arrow S to the HASTE sequence. In a physiological movement cycle formed by two adjacent troughs (for example, point A and point B) of the physiological signal curve 101, after the trigger signal is received from the PACE sequence, the HASTE sequence performs imaging scanning to obtain a single layer of imaging data 103. That is, in each respiratory cycle, the HASTE sequence only obtains one layer of imaging data. It may be seen that other time periods in the physiological movement cycle are not utilized, and consequently, the scanning speed is slow and the imaging time is long.

The above are defects in the prior art. After further research, it is noted that if the single layer of imaging data is not obtained in the single physiological movement cycle, but a plurality of imaging data is obtained in the single physiological movement cycle, the scanning speed may be significantly increased, and thus the imaging time may be shortened.

Figure 2:
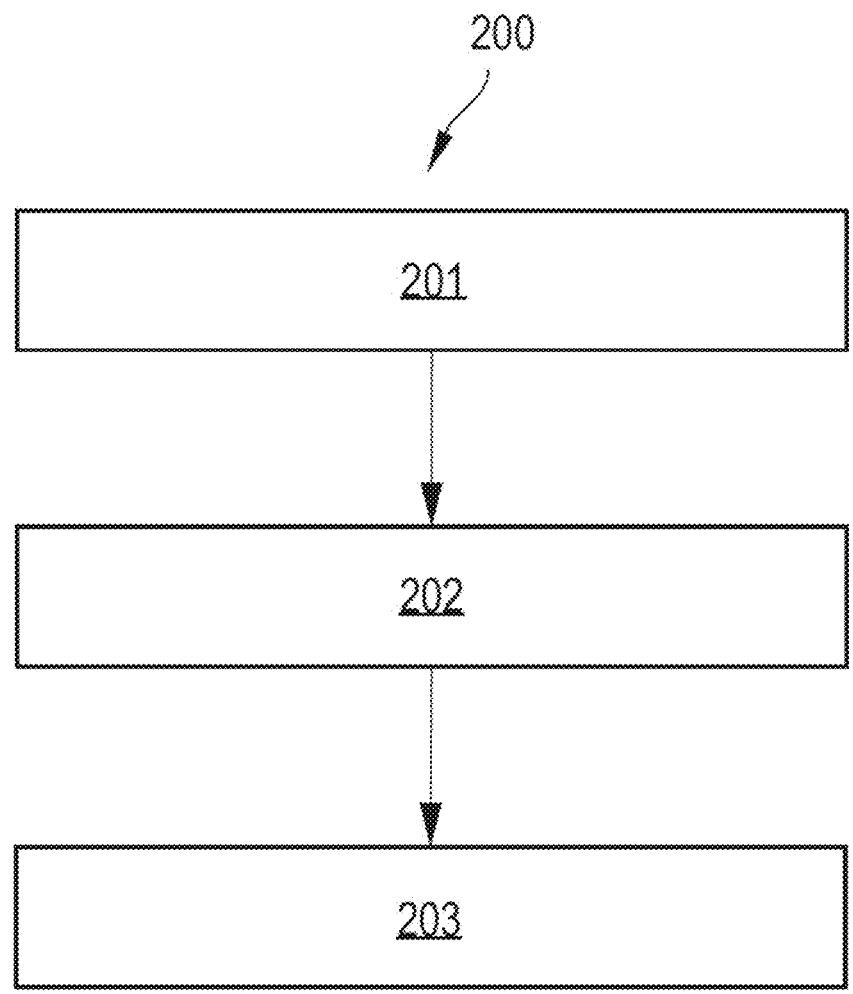
FIG. 2 is an example flowchart of a method for magnetic resonance imaging triggered by a PACE sequence according to an embodiment of the present disclosure.

FIG. 2 is an example flowchart of a method for magnetic resonance imaging triggered by a PACE sequence according to an embodiment of the present disclosure. As shown in FIG. 2, the method 200 for magnetic resonance imaging triggered by a PACE sequence comprises the following steps:

Step 201: repetition time and an acquisition window time of a single-shot fast spin echo sequence are determined.

In an embodiment, the single-shot fast spin echo sequence may be implemented as a HASTE sequence, a TSE-SSH sequence, an SS-FSE sequence, etc.

The repetition time of the single-shot fast spin echo sequence is a time span between an application moment of an excitation pulse and an application moment of the next excitation pulse, which determines a recovery degree of a longitudinal magnetization vector between these two excitation pulses. That is, the repetition time of the single-shot fast spin echo sequence is a time interval between repeated radio frequency pulses in the single-shot fast spin echo sequence.

A user may set the repetition time independently. For example, on the basis of the user setting the resolution of an imaged image, the user indirectly sets the repetition time. Generally, the higher the set resolution is, the longer the repetition time.

The acquisition window time is the scanning (that is, data acquisition) time of the single-shot fast spin echo sequence in a physiological movement cycle. All physiological movement cycles have the same acquisition window time. The start point of the acquisition window time is the moment when the single-shot fast spin echo sequence receives the trigger signal from the PACE sequence, and the end point of the acquisition window time may be any moment before the end moment of a physiological movement cycle.

In an embodiment, the acquisition window time applicable to all users may be determined on the basis of the user settings. For example, with the consideration that physiological movement cycles of most people are usually between 2 s and 4 s, the acquisition window time may be set between 1 s and 2 s. At this time, the acquisition window time is applicable to all the users.

In an embodiment, the acquisition window time applicable to a user may be determined on the basis of personalized respiratory features of the user. For example, the PACE sequence is applied to detect a physiological signal curve of the user; the physiological movement cycle of the user is determined on the basis of the physiological signal curve of the user; and the acquisition window time of the user is determined on the basis of the physiological movement cycle of the user. Preferably, half of the physiological movement cycle is set as the acquisition window time of the user. For example, it is assumed that the PACE sequence detects that the physiological movement cycle of the user is 2.4 s, and then the acquisition window time of the user may be set to 1.2 s.

Typical examples of the single-shot fast spin echo sequence, the repetition time and the acquisition window time are exemplarily described above, and those skilled in the art may realize that the description is merely exemplary and is not used to limit the scope of protection of the embodiment of the present disclosure.

Step 202: the maximum imaging layer number N in each physiological movement cycle is determined on the basis of the acquisition window time and the repetition time, where N is a positive integer greater than or equal to 2.

Herein, the maximum imaging layer number N is a maximum number of imaging layers that may be collected in each physiological movement cycle.

In an embodiment, the maximum imaging layer number N is determined, where N=int(TA/TR), where TR is the repetition time, TA is the acquisition window time, and int(TA/TR) is a rounded value of (TA/TR).

For example, it is assumed that the repetition time TR is 400 ms and TA is 1.3 s, and then TA/TR=1.3 (s)/400 (ms)=3.25, int(TA/TR)=3, and the maximum imaging layer number N is equal to 3.

For another example, it is assumed that the repetition time TR is 500 ms and TA is 1.3 s, and then TA/TR=1.3 (s)/500 (ms)=2.6, int(TA/TR)=2, and the maximum imaging layer number N is equal to 2.

Step 203: the single-shot fast spin echo sequence is enabled to obtain M layers of imaging data within an acquisition window time of at least one physiological movement cycle when the PACE sequence generates a trigger signal, where M is a positive integer greater than or equal to 2 and less than or equal to N. The value of M may be set by the user independently or randomly determined by a control host of a magnetic resonance imaging system.

In an embodiment, the number K of physiological movement cycles is determined when a predetermined total imaging layer number L is not divisible by M, where K=(int(L/M)+1), and int(L/M) is a rounded value of (L/M); the single-shot fast spin echo sequence is enabled to obtain M layers of imaging data within an acquisition window time of each physiological movement cycle from the first physiological movement cycle to a $(K-1)^{th}$ physiological movement cycle; and the single-shot fast spin echo sequence is enabled to obtain (L−(K−1)*M) layers of imaging data in a $K^{th}$ physiological movement cycle.

That M may be any positive integer less than or equal to N when the predetermined total imaging layer number L is not divisible by M comprises the following cases:

Case (I): M is less than N.

Example 1: it is assumed that the predetermined total imaging layer number L is 25 and the maximum imaging layer number N determined in step 202 is 3, and then M is a positive integer less than 3 and greater than or equal to 2, and is specifically 2. In this case, the number of physiological movement cycles K=(int(L/M)+1)=int(25/2)+1=13 is determined. Therefore, all physiological movement cycles comprise the first physiological movement cycle, the second physiological movement cycle, the third physiological movement cycle, . . . , and the $13^{th}$ physiological movement cycle that are in ascending order on the timeline. Among the cycles: in the first physiological movement cycle, two scans are performed; in the second physiological movement cycle, two scans are performed; in the third physiological movement cycle, two scans are performed; . . . ; and in the $12^{th}$ physiological movement cycle, two scans are performed. Further, in the $13^{th}$ physiological movement cycle, ((L−(K−1)*M))=1 scan is performed.

Example 2: it is assumed that the predetermined total imaging layer number L is 25 and the maximum imaging layer number N determined in step 202 is 4, and then M may be a positive integer less than 4 and greater than or equal to 2, for example, 2 or 3, and M is assumed to be 3. In this case, the number of physiological movement cycles K=int(L/M)+1=int(25/3)+1=9 is determined, that is, the number of physiological movement cycles is 9. Therefore, all physiological movement cycles comprise the first physiological movement cycle, the second physiological movement cycle, the third physiological movement cycle, . . . , and the ninth physiological movement cycle that are in ascending order on the timeline. Among the cycles: in the first physiological movement cycle, three scans are performed; in the second physiological movement cycle, three scans are performed; in the third physiological movement cycle, three scans are performed; . . . ; and in the eighth physiological movement cycle, three scans are performed. Further, in the ninth physiological movement cycle, ((L−(K−1)*M))=1 scan is performed.

Case (II): M is equal to N.

Example 1: it is assumed that the predetermined total imaging layer number L is 25 and the maximum imaging layer number N determined in step 202 is 3. M is equal to N, and is specifically 3. In this case, the number of physiological movement cycles K=int(L/M)+1=int(25/3)+1=9 is determined, that is, the number of physiological movement cycles is 9. Therefore, all physiological movement cycles comprise the first physiological movement cycle, the second physiological movement cycle, the third physiological movement cycle, . . . , and the ninth physiological movement cycle that are in ascending order on the timeline. Among the cycles: in the first physiological movement cycle, three scans are performed; in the second physiological movement cycle, three scans are performed; in the third physiological movement cycle, three scans are performed; . . . in the eighth physiological movement cycle, three scans are performed. Further, in the ninth physiological movement cycle, ((L−(K−1)*M))=1 scan is performed.

Example 2: it is assumed that the predetermined total imaging layer number L is 30 and the maximum imaging layer number N determined in step 202 is 4. M is equal to N, and is specifically 4. In this case, the number of physiological movement cycles K=int(L/M)+1=int(30/4)+1=8 is determined, that is, the number of physiological movement cycles is 8. Therefore, all physiological movement cycles comprise the first physiological movement cycle, the second physiological movement cycle, the third physiological movement cycle, . . . , and the eighth physiological movement cycle that are in ascending order on the timeline. Among the cycles: in the first physiological movement cycle, four scans are performed; in the second physiological movement cycle, four scans are performed; in the third physiological movement cycle, four scans are performed; . . . ; and in the seventh physiological movement cycle, four scans are performed. Further, in the eighth physiological movement cycle, ((L−(K−1)*M))=2 scans are performed.

In an embodiment, the number K of physiological movement cycles is determined when a predetermined total imaging layer number L is divisible by M, where K=(L/M), and the single-shot fast spin echo sequence is enabled to obtain M layers of imaging data within an acquisition window time of each physiological movement cycle from the first physiological movement cycle to a $K^{th}$ physiological movement cycle.

That M may be any positive integer less than or equal to N when the predetermined total imaging layer number L is divisible by M comprises the following cases:

Case (I): M is less than N.

Example 1: it is assumed that the predetermined total imaging layer number L is 24 and the maximum imaging layer number N determined in step 202 is 3, and then M is a positive integer less than 3 and greater than or equal to 2, and is specifically 2. In this case, the number of physiological movement cycles K=24/2=12 is determined, that is, the number of physiological movement cycles is 12. Therefore, all physiological movement cycles comprise the first physiological movement cycle, the second physiological movement cycle, the third physiological movement cycle, . . . , and the $12^{th}$ physiological movement cycle that are in ascending order on the timeline. Among the cycles: in the first physiological movement cycle, two scans are performed; in the second physiological movement cycle, two scans are performed; in the third physiological movement cycle, two scans are performed; . . . ; and in the $12^{th}$ physiological movement cycle, two scans are performed.

Example 2: it is assumed that the predetermined total imaging layer number L is 24 and the maximum imaging layer number N determined in step 202 is 4, and then M may be a positive integer less than 4 and greater than or equal to 2, for example, 2 or 3, and M is assumed to be 3. In this case, the number of physiological movement cycles K=24/3=8 is determined, that is, the number of physiological movement cycles is 8. Therefore, all physiological movement cycles comprise the first physiological movement cycle, the second physiological movement cycle, the third physiological movement cycle, . . . , and the eighth physiological movement cycle that are in ascending order on the timeline. Among the cycles: in the first physiological movement cycle, three scans are performed; in the second physiological movement cycle, three scans are performed; in the third physiological movement cycle, three scans are performed; . . . ; and in the eighth physiological movement cycle, three scans are performed.

Case (II): M is equal to N.

Example 1: it is assumed that the predetermined total imaging layer number L is 30 and the maximum imaging layer number N determined in step 202 is 3. M is equal to N, and is specifically 3. In this case, the number of physiological movement cycles K=30/3=10 is determined, that is, the number of physiological movement cycles is 10. Therefore, all physiological movement cycles comprise the first physiological movement cycle, the second physiological movement cycle, the third physiological movement cycle, . . . , and the $10^{th}$ physiological movement cycle that are in ascending order on the timeline. Among the cycles: in the first physiological movement cycle, three scans are performed; in the second physiological movement cycle, three scans are performed; in the third physiological movement cycle, three scans are performed; . . . ; and in the $10^{th}$ physiological movement cycle, three scans are performed.

Example 2: it is assumed that the predetermined total imaging layer number L is 28 and the maximum imaging layer number N determined in step 202 is 4. M is equal to N, and is specifically 4. In this case, the number of physiological movement cycles K=28/4=7 is determined, that is, the number of physiological movement cycles is 7. Therefore, all physiological movement cycles comprise the first physiological movement cycle, the second physiological movement cycle, the third physiological movement cycle, . . . , and the seventh physiological movement cycle that are in ascending order on the timeline. Among the cycles: in the first physiological movement cycle, four scans are performed; in the second physiological movement cycle, four scans are performed; in the third physiological movement cycle, four scans are performed; . . . ; and in the seventh physiological movement cycle, four scans are performed.

The specific manner of performing M scans within the acquisition window time is exemplarily described above, and those skilled in the art may realize that the description is merely exemplary and is not used to limit the scope of protection of the embodiment of the present disclosure.

The layer numbers of M layers of imaging data obtained in the same physiological movement cycle may be staggered (e.g. staggered at equal intervals), so as to prevent data interference in the same physiological movement cycle. For example, it is assumed that there are four physiological movement cycles, and three scans are performed within the acquisition window time in each physiological movement cycle. Then, in the first physiological movement cycle, the first layer of imaging data, the fifth layer of imaging data, and the ninth layer of imaging data may be collected separately; in the second physiological movement cycle, the second layer of imaging data, the sixth layer of imaging data, and the tenth layer of imaging data may be collected separately; in the third physiological movement cycle, the third layer of imaging data, the seventh layer of imaging data, and the eleventh layer of imaging data may be collected separately; and in the fourth physiological movement cycle, the fourth layer of imaging data, the eighth layer of imaging data, and the twelfth layer of imaging data may be collected separately.

Typical examples of mutually staggered layer numbers of M layers of imaging data are exemplarily described above, and those skilled in the art may realize that the description is merely exemplary and is not used to limit the scope of protection of the embodiment of the present disclosure.

The single-shot fast spin echo sequence being particularly implemented as a HASTE sequence is taken as an example for description of the embodiment of the present disclosure below.

Figure 3:
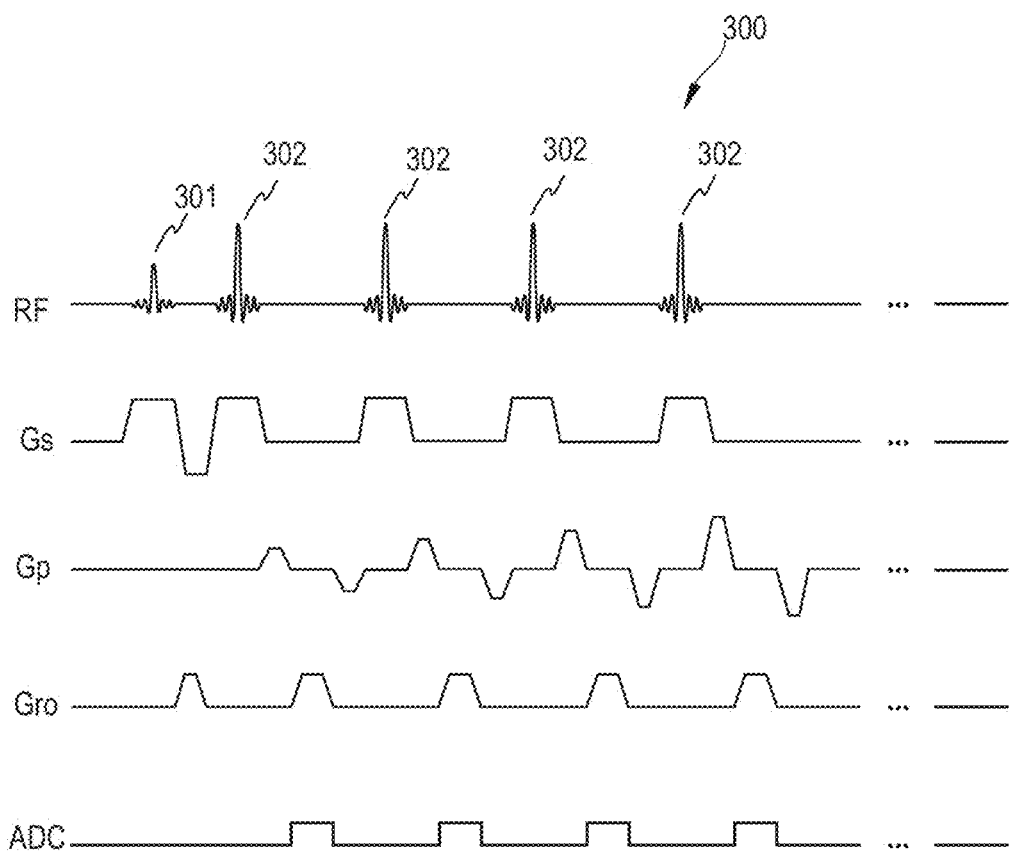
FIG. 3 is an example schematic diagram of obtaining a single layer of imaging data by a HASTE sequence according to an embodiment of the present disclosure.

FIG. 3 is an example schematic diagram of obtaining a single layer of imaging data by a HASTE sequence according to an embodiment of the present disclosure. In FIG. 3, an execution sequence of a radio frequency (RF) pulse, a slice selection gradient (Gs), a phase encoding gradient (Gp), a readout gradient (Gro), and analog-to-digital conversion (ADC) on the timeline is marked from top to bottom. ADC is the data acquisition step.

First step: a 90-degree radio frequency excitation pulse 301 is applied to the RF, and a slice selection gradient is applied in a Gs direction at the same time, so as to turn a magnetization vector in the selected slice to a transverse plane.

Second step: then, a compensation gradient is applied in the Gs direction to compensate for a disperse phase of the magnetization vector caused by the slice selection gradient over the period from the center of the excitation pulse to the end of the pulse, and a pre-disperse phase gradient is applied in a Gro direction at the same time.

Third step: a 180-degree radio frequency echo refocusing pulse 302 is applied to the RF, and a slice selection gradient is applied in the Gs direction at the same time, such that the magnetization vector in the selected slice refocuses in the middle of the following two 180-degree radio frequency echo refocusing pulses to form an echo. Then a phase encoding gradient is applied in a Gp direction.

Fourth step: a readout gradient is applied in the Gro direction while data is acquired on the ADC, and then a gradient opposite to the above-mentioned phase encoding gradient is applied in the Gs direction, so as to cancel the effect of the previous phase encoding gradient.

Fifth Step: according to preset resolution in a phase encoding direction, the third step and the fourth step are repeatedly executed until a complete layer of data is completely acquired. Then the first step to the fifth step are repeated to collect the next layer of data.

It may be seen that the HASTE sequence is a single-shot fast imaging sequence which may obtain a complete layer of images with only one shot (with one 90-degree excitation pulse).

When the resolution of an imaged image is 256*256, the number of radio frequency echo refocusing pulses 302 is 136; when the resolution of the imaged image is 128*128, the number of radio frequency echo refocusing pulses 302 is 72; and when the resolution of the imaged image is 320*320, the number of radio frequency echo refocusing pulses 302 is 184. It may be seen that by setting different resolutions, the number of radio frequency echo refocusing pulses 302 may be changed, thus changing the repetition time of the HASTE sequence.

Figure 4:
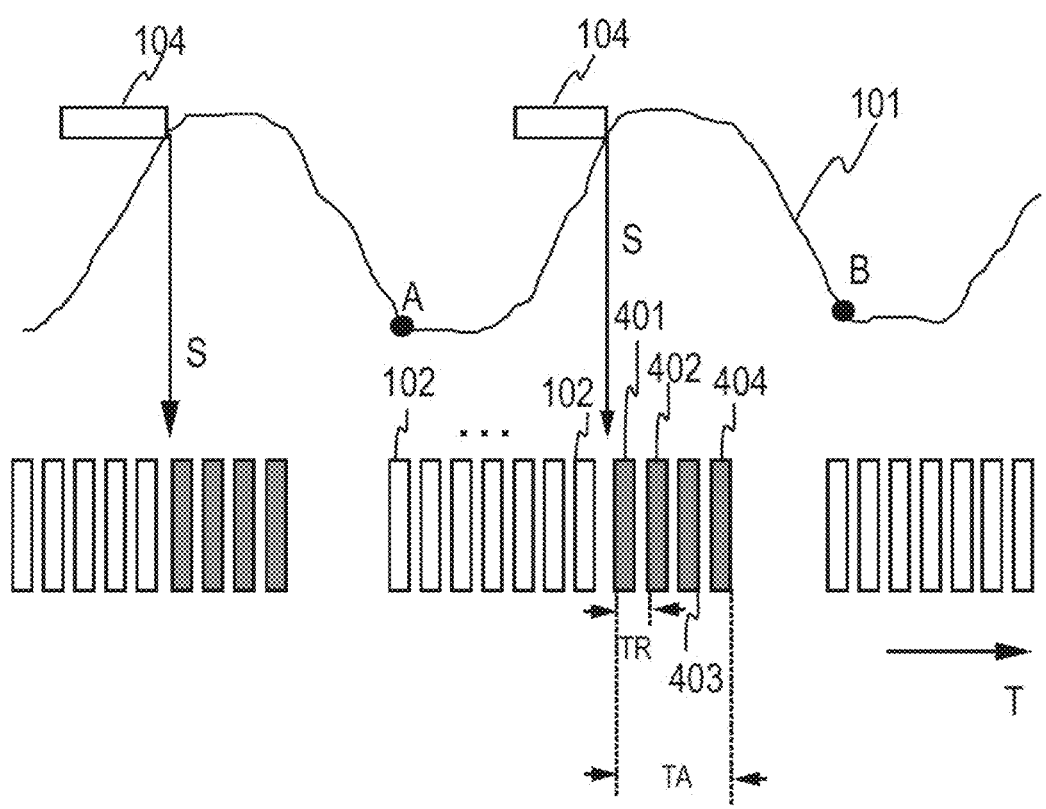
FIG. 4 is an example schematic diagram of obtaining imaging data by a HASTE sequence triggered by a PACE sequence according to an embodiment of the present disclosure.

FIG. 4 is an example schematic diagram of obtaining imaging data by a HASTE sequence triggered by a PACE sequence according to an embodiment of the present disclosure.

It may be seen from FIG. 4 that on a timeline T, a physiological signal curve 101 comprising a plurality of physiological movement cycles (such as respiratory cycles) extends periodically. In each physiological movement cycle, before the PACE sequence sends a trigger signal, a navigation sequence 102 is executed. When a receiving window 104 of the PACE sequence comes into contact with the physiological signal curve 101, the PACE sequence sends the trigger signal as shown by arrow S to the HASTE sequence. It is assumed that the maximum imaging layer number N determined on the basis of the repetition time TR and the acquisition window time TA is 4, and M is equal to N.

In a physiological movement cycle (for example, a respiratory cycle) formed by two adjacent troughs (for example, point A and point B) of the physiological signal curve 101, after the trigger signal is received from the PACE sequence, the HASTE sequence performs imaging scanning to obtain a first single layer of imaging data 401, a second single layer of imaging data 402, a third single layer of imaging data 403 and a fourth single layer of imaging data 404. That is, after the trigger signal is received, the HASTE sequence executes the execution process 300 of obtaining a single layer of imaging data by the HASTE sequence as shown in FIG. 3 four times within one physiological movement cycle to obtain four layers of imaging data.

In addition, it may be seen from FIG. 4 that the start point of TA may be the moment when the HASTE sequence receives the trigger signal from the PACE sequence, and the end point of TA may be any moment before the end moment of a physiological movement cycle.

In FIGS. 3 to 4, the single-shot fast imaging sequence being implemented as a HASTE sequence is taken as an example for description, and those skilled in the art may realize that the single-shot fast imaging sequence may also be implemented as a TSE-SSH sequence, an SS-FSE sequence, etc.

On the basis of the description above, an embodiment of the present disclosure further proposes an apparatus for magnetic resonance imaging triggered by a PACE sequence.

Figure 5:
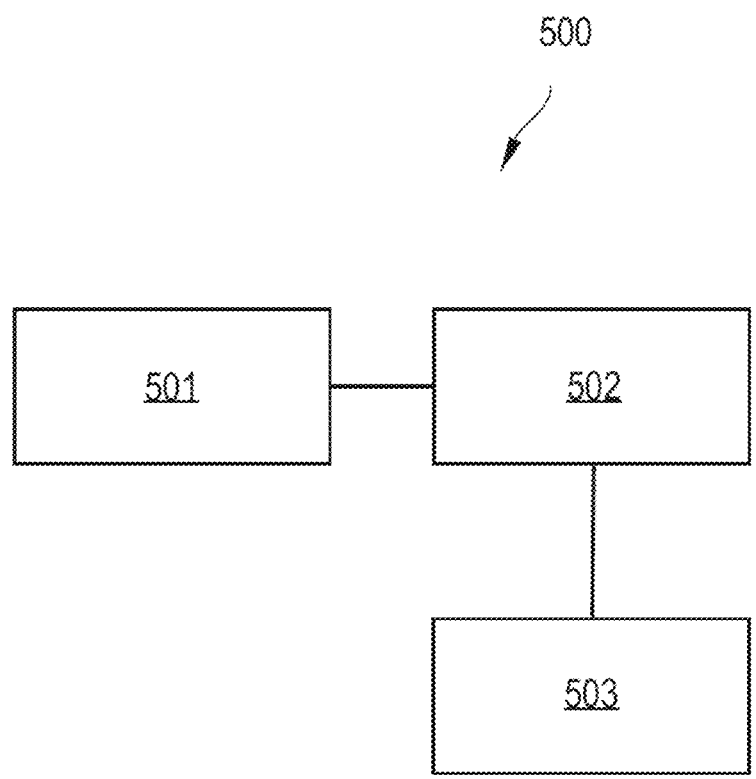
FIG. 5 is an example structural diagram of an apparatus for magnetic resonance imaging triggered by a PACE sequence according to an embodiment of the present disclosure.

FIG. 5 is an example structural diagram of an apparatus for magnetic resonance imaging triggered by a PACE sequence according to an embodiment of the present disclosure.

As shown in FIG. 5, the apparatus 500 for magnetic resonance imaging triggered by a PACE sequence comprises:
   a time determination module 501 (e.g. time determination circuitry, which may comprise one or more processors, processing circuitry, etc.) configured to determine repetition time and an acquisition window time of a single-shot fast spin echo sequence;
   a maximum imaging layer number determination module 502 (e.g. maximum imaging layer number determination circuitry, which may comprise one or more processors, processing circuitry, etc.) configured to determine the maximum imaging layer number N in each physiological movement cycle on the basis of the acquisition window time and the repetition time, where N is a positive integer greater than or equal to 2; and
   an imaging data obtaining module 503 (e.g. imaging data acquisition circuitry, which may comprise one or more processors, processing circuitry, etc.) configured to enable the single-shot fast spin echo sequence to obtain M layers of imaging data within at least one acquisition window time when a trigger signal is received from the PACE sequence, where M is a positive integer greater than or equal to 2 and less than or equal to N.

In an embodiment, the time determination module 501 is configured to apply the PACE sequence to detect a physiological signal curve; determine the physiological movement cycle on the basis of the physiological signal curve; and determine the acquisition window time on the basis of the physiological movement cycle.

In an embodiment, the maximum imaging layer number determination module 502 is configured to determine the maximum imaging layer number N, where N=int(TA/TR); and where TR is the repetition time, TA is the acquisition window time, and int(TA/TR) is a rounded value of (TA/TR).

In an embodiment, the imaging data obtaining module 503 is configured to determine the number K of physiological movement cycles when a predetermined total imaging layer number L is not divisible by M, where K=(int(L/M)+1), and int(L/M) is a rounded value of (L/M); enable the single-shot fast spin echo sequence to obtain M layers of imaging data within an acquisition window time of each physiological movement cycle from the first physiological movement cycle to a $(K-1)^{th}$ physiological movement cycle; and enable the single-shot fast spin echo sequence to obtain $(L-(K-1)*M)$ layers of imaging data in a $K^{th}$ physiological movement cycle; or determine the number K of physiological movement cycles when a predetermined total imaging layer number L is divisible by M, where $K=(L/M)$; and enable the single-shot fast spin echo sequence to obtain M layers of imaging data within an acquisition window time of each physiological movement cycle from the first physiological movement cycle to a $K^{th}$ physiological movement cycle.

On the basis of the description above, an embodiment of the present disclosure further proposes a control host of a magnetic resonance imaging system.

Figure 6:
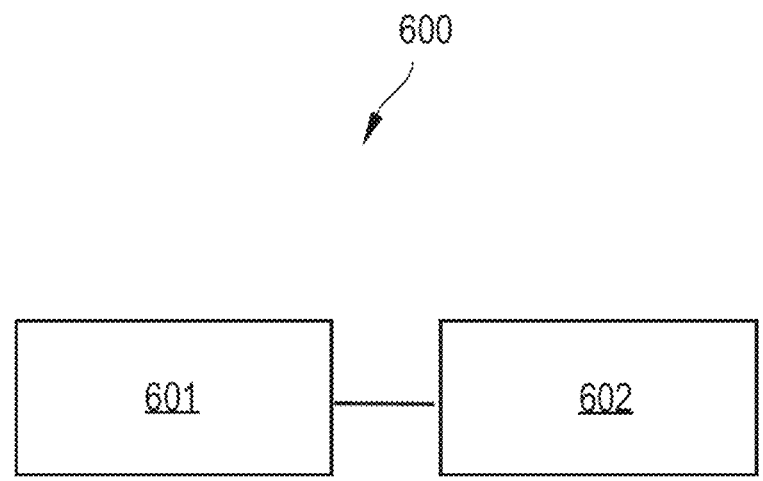
FIG. 6 is an example structural diagram of a control host of a magnetic resonance imaging system according to an embodiment of the present disclosure.

FIG. 6 is an example structural diagram of a control host of a magnetic resonance imaging system according to an embodiment of the present disclosure.

As shown in FIG. 6, the control host 600 (e.g. a control computer, controller, control circuitry, etc.) comprises a processor 601, a memory 602, and a computer program stored on the memory 602 and operable on the processor 601. The computer program, when executed by the processor 601, implements the method for magnetic resonance imaging triggered by a PACE sequence as described in any of the above.

The memory 602 may be specifically implemented as non-transitory computer readable media and/or various storage media such as an electrically erasable programmable read-only memory (EEPROM), a flash memory, a programmable read-only memory (PROM), etc. The processor 601 may be implemented to comprise one or more central processing units or one or more field programmable gate arrays, among which the field programmable gate arrays integrate one or more central processing unit cores. Specifically, the central processing unit or the central processing unit core may be implemented as a CPU, a microcontroller unit (MCU), a digital signal processor (DSP), etc.

To sum up, in the embodiments of the present disclosure, the repetition time and the acquisition window time of the single-shot fast spin echo sequence are determined; the maximum imaging layer number N in each physiological movement cycle is determined on the basis of the acquisition window time and the repetition time, where N is a positive integer greater than or equal to 2; and the single-shot fast spin echo sequence is enabled to obtain M layers of imaging data within at least one acquisition window time when the PACE sequence generates a trigger signal, where M is a positive integer greater than or equal to 2 and less than or equal to N. It may be seen that, according to the embodiment of the present disclosure, a plurality of layers of imaging data is obtained within a single acquisition window time, thereby increasing the scanning speed and shortening imaging time.

In addition, in the embodiments of the present disclosure, the acquisition window time may be determined on the basis of the physiological signal curve detected by the PACE sequence, thereby improving the accuracy of the acquisition window time.

Moreover, according to embodiments of the present disclosure, different processing manners of acquisition of a plurality of layers of imaging data within the acquisition window time are realized in consideration of different conditions of whether the total imaging layer number is divisible by M.

By abiding by an application program interface of a certain specification, the prospective electrocardio triggering method proposed by the embodiments of the present disclosure may be written as a plug-in program installed in the control host for the magnetic resonance imaging, a personal computer, a mobile terminal, etc., or packaged into an application program for users to download and use by themselves.

The prospective electrocardio triggering method proposed by the embodiments of the present disclosure may be stored on various storage media by means of instruction or instruction set storage. These storage media include, but are not limited to, floppy disks, optical discs, digital versatile discs (DVD), hard disks, flash memories, etc. In addition, the prospective electrocardio triggering method proposed by the embodiment of the present disclosure may also be applied to storage media based on Nand flash, such as a USB flash drive, compact flash (CF), a secure digital memory card (SD), a secure digital high capacity (SDHC) card, a multimedia card (MMC), a SmartMedia (SM) card, a memory stick, and an xd-picture card (xD).

The above description describes example embodiments of the present disclosure, and is not intended to limit the scope of protection of the present disclosure. Any modifications, equivalent substitutions, improvements, etc. made within the spirit and principles of the present disclosure shall fall under the scope of protection of the present disclosure.

What is claimed is:

1. A method for magnetic resonance imaging triggered by a prospective acquisition correction sequence, comprising:
   determining, via one or more processors, a repetition time and an acquisition window time of a single-shot fast spin echo sequence;
   determining, via the one or more processors, a maximum imaging layer number N in each one of a plurality of physiological movement cycles based upon the acquisition window time and the repetition time,
   wherein N is a positive integer greater than or equal to 2; and
   enabling, via the one or more processors, the single-shot fast spin echo sequence to obtain M layers of imaging data within at least one acquisition window time when the prospective acquisition correction sequence generates a trigger signal,
   wherein M is a positive integer greater than or equal to 2 and less than or equal to N, and
   wherein the enabling the single-shot fast spin echo sequence to obtain M layers of imaging data within at least one acquisition window time comprises:
      determining a number K of the plurality of physiological movement cycles when a predetermined total imaging layer number L is not divisible by M, with $K=(int(L/M)+1)$, and $int(L/M)$ represents a rounded value of $(L/M)$;
      enabling the single-shot fast spin echo sequence to obtain M layers of imaging data within an acquisition window time of each physiological movement cycle from a first physiological movement cycle to a $(K-1)$th physiological movement cycle; and
      enabling the single-shot fast spin echo sequence to obtain $(L-(K-1)*M)$ layers of imaging data in a Kth physiological movement cycle.

2. The method according to claim 1, wherein the determining the acquisition window time comprises:
   applying the prospective acquisition correction sequence to detect a physiological signal curve;
   determining a physiological movement cycle from among the plurality of physiological movement cycles based upon the physiological signal curve; and determining the acquisition window time based upon the physiological movement cycle.

3. The method according to claim 1, wherein the determining the maximum imaging layer number N in each physiological movement cycle comprises:
determining the maximum imaging layer number N by evaluating:

$$N=\text{int}(TA/TR),$$

wherein TR represents the repetition time,
wherein TA represents the acquisition window time, and
wherein int(TA/TR) represents a rounded value of (TA/TR).

4. An apparatus for magnetic resonance imaging triggered by a prospective acquisition correction sequence, the apparatus comprising:
time determination circuitry configured to determine a repetition time and an acquisition window time of a single-shot fast spin echo sequence;
maximum imaging layer number determination circuitry configured to determine a maximum imaging layer number N in each one of a plurality of physiological movement cycles based upon the acquisition window time and the repetition time,
wherein N is a positive integer greater than or equal to 2; and
imaging data acquisition circuitry configured to enable the single-shot fast spin echo sequence to obtain M layers of imaging data within at least one acquisition window time when the prospective acquisition correction sequence generates a trigger signal,
wherein M is a positive integer greater than or equal to 2 and less than or equal to N, and
wherein the imaging data acquisition circuitry is configured to enable the single-shot fast spin echo sequence to obtain M layers of imaging data by:
determining a number K of the plurality of physiological movement cycles when a predetermined total imaging layer number L is not divisible by M, with K=(int(L/M)+1), and int(L/M) represents a rounded value of (L/M);
enabling the single-shot fast spin echo sequence to obtain M layers of imaging data within an acquisition window time of each physiological movement cycle from a first physiological movement cycle to a (K−1)th physiological movement cycle; and
enabling the single-shot fast spin echo sequence to obtain (L−(K−1)*M) layers of imaging data in a Kth physiological movement cycle.

5. The apparatus according to claim 4, wherein the time determination circuitry is configured to:
apply the prospective acquisition correction sequence to detect a physiological signal curve;
determine a physiological movement cycle from among the plurality of physiological movement cycles based upon the physiological signal curve; and
determine the acquisition window time based upon the physiological movement cycle.

6. The apparatus according to claim 4, wherein:
the maximum imaging layer number determination circuitry is configured to determine the maximum imaging layer number N by evaluating:

$$N=\text{int}(TA/TR),$$

wherein TR represents the repetition time,
wherein TA represents the acquisition window time, and
wherein int(TA/TR) represents a rounded value of (TA/TR).

7. A computer-readable storage medium having instructions stored thereon that, when executed by one or more processors associated with a magnetic resonance imaging apparatus for magnetic resonance imaging triggered by a prospective acquisition correction sequence, cause the magnetic resonance imaging apparatus to:
determine a repetition time and an acquisition window time of a single-shot fast spin echo sequence;
determine a maximum imaging layer number N in each one of a plurality of physiological movement cycles based upon the acquisition window time and the repetition time,
wherein N is a positive integer greater than or equal to 2; and
enable the single-shot fast spin echo sequence to obtain M layers of imaging data within at least one acquisition window time when the prospective acquisition correction sequence generates a trigger signal,
wherein M is a positive integer greater than or equal to 2 and less than or equal to N, and
wherein the instructions cause the cause the magnetic resonance imaging apparatus to enable the single-shot fast spin echo sequence to obtain M layers of imaging data within at least one acquisition window time by:
determining a number K of the plurality of physiological movement cycles when a predetermined total imaging layer number L is not divisible by M, with K=(int(L/M)+1), and int(L/M) represents a rounded value of (L/M);
enabling the single-shot fast spin echo sequence to obtain M layers of imaging data within an acquisition window time of each physiological movement cycle from a first physiological movement cycle to a (K−1)th physiological movement cycle; and
enabling the single-shot fast spin echo sequence to obtain (L−(K−1)*M) layers of imaging data in a Kth physiological movement cycle.

8. The computer-readable storage medium according to claim 7, wherein the instructions cause the magnetic resonance imaging apparatus to determine the acquisition window time by:
applying the prospective acquisition correction sequence to detect a physiological signal curve;
determining a physiological movement cycle from among the plurality of physiological movement cycles based upon the physiological signal curve; and
determining the acquisition window time based upon the physiological movement cycle.

9. The computer-readable storage medium according to claim 7, wherein the instructions cause the magnetic resonance imaging apparatus to determine the maximum imaging layer number N in each physiological movement cycle by:
determining the maximum imaging layer number N by evaluating:

$$N=\text{int}(TA/TR),$$

wherein TR represents the repetition time,
wherein TA represents the acquisition window time, and
wherein int(TA/TR) represents a rounded value of (TA/TR).

10. A method for magnetic resonance imaging triggered by a prospective acquisition correction sequence, comprising:

determining, via one or more processors, a repetition time and an acquisition window time of a single-shot fast spin echo sequence;

determining, via the one or more processors, a maximum imaging layer number N in each one of a plurality of physiological movement cycles based upon the acquisition window time and the repetition time, wherein N is a positive integer greater than or equal to 2; and enabling, via the one or more processors, the single-shot fast spin echo sequence to obtain M layers of imaging data within at least one acquisition window time when the prospective acquisition correction sequence generates a trigger signal, wherein M is a positive integer greater than or equal to 2 and less than or equal to N, wherein enabling the single-shot fast spin echo sequence to obtain M layers of imaging data within at least one acquisition window time comprises:

determining a number K of the plurality of physiological movement cycles when a predetermined total imaging layer number L is divisible by M, with K=(L/M); and enabling the single-shot fast spin echo sequence to obtain M layers of imaging data within an acquisition window time of each physiological movement cycle from a first physiological movement cycle to a Kth physiological movement cycle.

11. The method according to claim 10, wherein the determining the acquisition window time comprises:

applying the prospective acquisition correction sequence to detect a physiological signal curve;

determining a physiological movement cycle from among the plurality of physiological movement cycles based upon the physiological signal curve; and determining the acquisition window time based upon the physiological movement cycle.

12. The method according to claim 10, wherein determining the maximum imaging layer number N in each physiological movement cycle comprises:

determining the maximum imaging layer number N by evaluating:

$N=\text{int}(TA/TR)$, wherein TR represents the repetition time, wherein TA represents the acquisition window time, and wherein int(TA/TR) represents a rounded value of (TA/TR).

13. An apparatus for magnetic resonance imaging triggered by a prospective acquisition correction sequence, the apparatus comprising:

time determination circuitry configured to determine a repetition time and an acquisition window time of a single-shot fast spin echo sequence;

maximum imaging layer number determination circuitry configured to determine a maximum imaging layer number N in each one of a plurality of physiological movement cycles based upon the acquisition window time and the repetition time, wherein N is a positive integer greater than or equal to 2; and imaging data acquisition circuitry configured to enable the single-shot fast spin echo sequence to obtain M layers of imaging data within at least one acquisition window time when the prospective acquisition correction sequence generates a trigger signal, wherein M is a positive integer greater than or equal to 2 and less than or equal to N, and wherein the imaging data acquisition circuitry is configured to enable the single-shot fast spin echo sequence to obtain M layers of imaging data by:

determining a number K of the plurality of physiological movement cycles when a predetermined total imaging layer number L is divisible by M, with K=(L/M); and enabling the single-shot fast spin echo sequence to obtain M layers of imaging data within an acquisition window time of each physiological movement cycle from a first physiological movement cycle to a Kth physiological movement cycle.

14. The apparatus according to claim 13, wherein the time determination circuitry is configured to:

apply the prospective acquisition correction sequence to detect a physiological signal curve;

determine a physiological movement cycle from among the plurality of physiological movement cycles based upon the physiological signal curve; and determine the acquisition window time based upon the physiological movement cycle.

15. The apparatus according to claim 13, wherein:

the maximum imaging layer number determination circuitry is configured to determine the maximum imaging layer number N by evaluating:

$N=\text{int}(TA/TR)$, wherein TR represents the repetition time, wherein TA represents the acquisition window time, and wherein int(TA/TR) represents a rounded value of (TA/TR).

16. A computer-readable storage medium having instructions stored thereon that, when executed by one or more processors associated with a magnetic resonance imaging apparatus for magnetic resonance imaging triggered by a prospective acquisition correction sequence, cause the magnetic resonance imaging apparatus to:

determine a repetition time and an acquisition window time of a single-shot fast spin echo sequence;

determine a maximum imaging layer number N in each one of a plurality of physiological movement cycles based upon the acquisition window time and the repetition time, wherein N is a positive integer greater than or equal to 2; and enable the single-shot fast spin echo sequence to obtain M layers of imaging data within at least one acquisition window time when the prospective acquisition correction sequence generates a trigger signal, wherein M is a positive integer greater than or equal to 2 and less than or equal to N, and wherein the instructions cause the cause the magnetic resonance imaging apparatus to enable the single-shot fast spin echo sequence to obtain M layers of imaging data within at least one acquisition window time by:

determining a number K of the plurality of physiological movement cycles when a predetermined total imaging layer number L is divisible by M, with K=(L/M); and enabling the single-shot fast spin echo sequence to obtain M layers of imaging data within an acquisition window time of each physiological movement cycle from a first physiological movement cycle to a Kth physiological movement cycle.

17. The computer-readable storage medium according to claim 16, wherein the instructions cause the magnetic resonance imaging apparatus to determine the acquisition window time by:
   applying the prospective acquisition correction sequence to detect a physiological signal curve;
   determining a physiological movement cycle from among the plurality of physiological movement cycles based upon the physiological signal curve; and
   determining the acquisition window time based upon the physiological movement cycle.

18. The computer-readable storage medium according to claim 16, wherein the instructions cause the magnetic resonance imaging apparatus to determine the maximum imaging layer number N in each physiological movement cycle by:
   determining the maximum imaging layer number N by evaluating:

$$N=\text{int}(TA/TR),$$

wherein TR represents the repetition time,
   wherein TA represents the acquisition window time, and
   wherein int(TA/TR) represents a rounded value of (TA/TR).

* * * * *